United States Patent [19]

Furutani et al.

[11] Patent Number: 5,166,318
[45] Date of Patent: Nov. 24, 1992

[54] POLYPEPTIDE HAVING THROMBIN INHIBITING ACTIVITY

[75] Inventors: Yoshio Furutani, Miura; Masaru Honjo, Mobara; Akira Nakayama, Mobara; Koichi Kawamura, Mobara; Kazunori Ando, Mobara; Michiko Hori, Mobara; Keiko Fukazawa, Nagareyama, all of Japan

[73] Assignee: Mitsui Toatsu Chemicals, Incorporated, Tokyo, Japan

[21] Appl. No.: 531,403

[22] Filed: Jun. 4, 1990

[30] Foreign Application Priority Data

Jun. 9, 1989 [JP] Japan ................... 1-145489

[51] Int. Cl.$^5$ .............. A61K 35/14; A61K 37/02; C12P 21/00; C12N 15/00
[52] U.S. Cl. ..................... 530/381; 530/300; 435/68.11; 435/172.3; 435/252.31
[58] Field of Search .............. 530/300, 381; 435/68.1, 435/172.3, 252.31

[56] References Cited

FOREIGN PATENT DOCUMENTS

| 0151760 | 2/1985 | European Pat. Off. |
| 2611723 | 11/1988 | France |
| 2171703 | 7/1986 | United Kingdom |

OTHER PUBLICATIONS

Wallace et al. Biochemistry vol. 28 pp. 10079-10084 (1989).
Harvey et al, Proc. Natl. Acad. Sci. USA vol. 83 pp. 1084-1088 (1986).
Dodt et al. FEBS. vol 202 pp. 373-377 (1986).
Honjo et al J. Biotechnol. vol. 4, pp. 63-71.
Nakayama et al, Journal of Biotechnology, vol. 8, No. 2, pp. 123-134, 1988.

*Primary Examiner*—Joan Ellis
*Attorney, Agent, or Firm*—Nixon & Vanderhye

[57] ABSTRACT

Modified HV1-type hirudinin which valine at the N-terminal end of the HV1-type hirudin and aspartic acid at the 5th residue of the N-terminal end were replaced with alanine and glutamic acid, respectively. A secretion plasmid into which a DNA sequence coding for a precursor with an addition of a secretion signal of neutral protease of *Bacillus amyloliquefaciens* at the N-terminal end of this modified HV1-type hirudin is integrated is introduced into bacteria of the genus Bacillus and the precursor is expressed intracellularly. The modified HV1-type hirudin can be efficiently secreted extracellularly while maintaining its high thrombin inhibiting activity.

2 Claims, 4 Drawing Sheets

POLYPEPTIDE HAVING THROMBIN INHIBITING ACTIVITY

BACKGROUND OF THE INVENTION

1. Field of the Invention

This invention relates to a polypeptide having thrombin inhibiting activity and to a process for the manufacture thereof.

2. Description of the Prior Art

Thrombosis has attracted considerable attention as a disease exhibiting a tendency to increase lately. A thrombus is a blood clot which is generated by coagulation in the blood stream and the clinical phenomena in which thrombi are formed is called thrombosis. It is known that the thrombi are frequently formed at sites where changes in the vascular endothelium, especially sclerotic or inflammatory changes, occur; furthermore, these lesions rapidly increase with aging, and consequently the worldwide increase in life span is one of the causes of the increase in the incidence of thrombosis. Thrombi are known to be formed due to the deposit of fibrin in the microvascular system as a result of the pathological activation of thrombin in the blood of the whole body.

Thrombosis leads to vascular constriction and obstruction due to thrombi, which result in ischemic lesions and infarction in major organs such as the heart, brain and lungs and cause functional disorders thereof. Furthermore, these kinds of thrombosis have lately attracted attention as developmental pathology of organic inflammations due to immunological mechanisms, such as nephritis and pneumonitis like and accessory lesions associated with transplantation of organs and vessel substitutes. Furthermore, disseminated intravascular coagulation (DIC) syndrome, known as a pathological state in which thrombi frequently occur mainly in the microvessels, attracts attention as a peculiar symptom. The concept of DIC was first suggested in 1960s; in those days, DIC was considered to be a very rare syndrome. However, it has lately been revealed that DIC is not peculiar; moreover, bleeding generated in the late stage of various disorders and various clinical symptoms which had been overlooked without being well understood as organic symptoms have been understood as a result of DIC.

Examples of clinical pathology of thromboses are cerebral apoplexy, cardiac infarction, deep phlebothrombosis, obstruction of an extremity artery, pulmonary thrombosis and fundus thrombosis. Both overall morbidity and mortality of these thromboses of various organs in individual special categories are said to be in the first rank among various diseases.

Therefore, the clinical and pathological significance of thrombosis is considered to magnify its importance daily.

Examples of known therapeutic agents for thrombosis are heparin which acts via antithrombin III and anti-vitamin K agents which inhibit biosynthesis of vitamin K dependent blood coagulation factors. Furthermore, another known thrombin inhibitor is a gabexate mesylate agent which is a non-peptide proteolytic inhibitor. Since this agent is also effective in inhibiting activity of enzymes such as plasmin, kallikrein and trypsin which have physiologically important significance, its use requires careful supervision.

Heparin, which has long been well known, is an antithrombin agent frequently used in the cases of thromboses represented by DIC; however, since its action is to accelerate anticoagulant activity of antithrombin III, heparin is considered to be ineffective for therapy in the cases where antithrombin III is decreased, for example in the cases of thromboses associated with DIC or nephrosis (see Reference 1). From these points of view, development of promising novel antithrombus agents for therapeutic uses is of great importance in therapeutic and prophylactic medicine.

Considerable hope is placed in HV1-type hirudin as an antithrombus agent having such pharmaceutical effects. The HV1-type hirudin is a polypeptide having thrombin inhibiting activity present in the salivary gland of medicinal leeches (Hirudo medicinalis). The HV1-type hirudin consists of 65 amino acid residues, and the presence of three intramolecular S—S bridges, which are essential for expression of thrombin inhibiting activity, is known as a configurational characteristic. In particular, the HV1-type hirudin has particularly high specificity in action against thrombin and prethrombin 2 (dissociation constant: $0.8 \times 10^{-10}$) (see Reference 2), and only the activated factor IV other than thrombin is inhibited. Namely, the HV1-type hirudin does not inhibit enzymes other than those related to blood coagulation. Furthermore, the HV1-type hirudin is said to be extremely low in toxicity, nonantigenic and readily excreted from the kidney in the urine in a form having biological activity (see Reference 3).

Considering these aspects, HV1-type hirudin has the potential to be used as a very valuable prophylactic or therapeutic agent for thromboses including DIC in place of conventional antithrombosis agents.

Before the availability of recombinant DNA techniques, HV1-type hirudin was produced by direct extraction from leeches. However, in this method, a large number of starved leeches were required to obtain only a small amount of hirudin, and a considerably complicated purification steps and time were needed to obtain a crude hirudin preparation. For example, just to obtain a crude hirudin preparation with the purity as low as 10% also containing various contaminant proteins derived from the leeches, other than the HV1-type hirudin, processing included heat extraction of the homogenate of leeches starved for 2 to 3 weeks, ethanol precipitation, acetone fractionating precipitation, adsorption and desorption using bentonite and isoelectric precipitation were required. Furthermore, in order to obtain the HV1-type hirudin in a pure form using this crude hirudin preparation, ECTEOLA cellulose column chromatography, Sephadex CM-25 column chromatography and gel filtration using Sephadex G-25 had to be carried out, and the yield is reported to be less than 0.001% (see Reference 4). Since it is impossible to obtain the hirudin in quantities as described above, the therapeutic utilization of the hirudin which can be expected from excellent characteristics thereof has not been achieved at present.

Recently, it is possible to produce a large amount of heterologous gene products employing microorganisms as hosts using recombinant DNA techniques by expressing heterologous genes which are not naturally present in the microorganisms.

Processes of producing substances using recombinant DNA techniques using microorganisms as hosts can be generally divided into two categories: intracellular production and extracellular excretive production.

In the case of intracellular production, heterologous gene products can be effectively produced in the cells; however, there are problems such as degradation of the heterologous gene products by intracellular proteases, formation of inclusion bodies observed in the case of mass quantity production, and addition of methionine, which is a start codon for transcription, to the amino-terminal of the heterologous gene products. According to current research, it has been revealed that these problems can be solved by causing the heterologous gene products to be secreted outside the cells (see Reference 5). Furthermore, in the case of the extracellular production, the desired heterologous gene products can be purified easily, and marked reduction in possible contamination of foreign substances can be advantageously attained.

As has been mentioned above, it is important to produce heterologous gene products and have them excreted, in terms of producing desired substances.

Intracellular and extracellular productions have been reported also regarding HV1-type hirudin. In the intracellular production of HV1-type hirudin using *Escherichia coli* as a host, HV1-type hirudin having as little as 0.2 mg/l A660 of thrombin inhibiting activity was reported to be accumulated (see Reference 6). Thus, the HV1-type hirudin was accumulated only in a small amount probably because of the accumulation of inactive hirudin where the S—S bond(s) which is essential for the expression of the thrombin inhibiting activity is not precisely crosslinked.

Where the expression is carried out within the cells to produce a preprotein in which a secretion signal is bound upstream of the N-terminal of HV1-type hirudin and the product is secreted outside the cells, problems due to the intracellular production can be avoided so that the HV1-type hirudin is expected to be secreted outside the cells.

From these points of view, the secretory productions of HV1-type hirudin using *E. coli* or yeasts as hosts have been reported. In the secretory production of HV1-type hirudin using *E. coli* as a host, particularly, H. Dodt et al. encountered a problem (see Reference 7). They tried to construct a secretion plasmid having a DNA sequence coding for the secretion signal of *E. coli* alkaline phosphatase, immediately followed by a DNA sequence coding for the mature HV1-type hirudin and then attempted secretion of HV1-type hirudin using *E. coli* as a host. In this case, a polypeptide with an addition of three amino acids upstream of the N-terminal of the HV1-type hirudin, other than the HV1-type hirudin, was secreted. The thrombin inhibiting activity of this polypeptide having the additional amino acids is only to about 1/500 that of HV1-type hirudin.

Furthermore, in the secretory production of heterologous gene products using yeasts as hosts, in particular, the problem that amino acid residues at the C-terminal of the heterologous gene products are deleted, has been reported (see Reference 8). In fact, also in the secretory production of HV1-type hirudin using yeasts as hosts, 10 mg of HV1-type hirudin was accumulated in 1 liter of culture (see Reference 9). However, in this case, the presence of hirudin having reduced thrombin inhibiting activity, in which one or two amino acid residues at the C-terminal of the HV1-type hirudin were missing, was reported (see Reference 10).

In order to solve these problems, investigations have been made on the secretory production of HV1-type hirudin using bacterial strains of the genus Bacillus, which are capable of secreting a large quantity of proteins and are often used as industrial microorganisms for enzymes, amino acids, nucleic acids and the like, based on considerable prior experience. In particular, investigations have been made on methods using *Bacillus subtilis* as a host, among the bacteria of the genus Bacillus, on which a large number of genetic, biological, molecular biological, and applied microbiological knowledge has been accumulated. There have been several reports on attempts regarding extracellular secretion of heterologous gene products using *Bacillus subtilis* having such characteristics (see References 11 and 12); however, it has also been reported that secretory production of a large amount of proteins derived from eukaryotic organisms using *Bacillus subtilis* is not necessarily easy (see Reference 13).

In order to accomplish effective secretion of a desired heterologous gene product, it is important to select a combination of a selected mature protein and a secretion signal. In particular, since the ligation structure arises between the heterologous gene product and the secretion signal, namely the amino acid sequence of the junction region greatly effects on the secretory efficiency and the function of the secreted heterologous gene products, it is important to decide what kind of amino acid sequence is used at this junction region.

Palva et al. (see Reference 14) and Schien et al. (see Reference 15) have reported the effect of the alteration of an original amino acid sequence of the secretion signal due to the junction region between the secretion signal and a heterologous protein on the efficiency of the secretive production of the heterologous protein.

For example, Palva et al. attempted to bind a DNA fragment coding for mature interferon (IFN) immediately after the region encoding Ala-Val containing a cleavage site of the secretion signal of alpha-amylase, a secretory protein, of *Bacillus amyloliquefacieno*, via a junction region consisting of 5 amino acid residues (Asn-Gly-Thr-Glu-Ala) to secrete human IFN. In this case, the secretion signal was removed, but it has been reported that the secreted interferon was a fusion protein secreted and accumulated in a form in which one amino acid (Val) or 6 amino acids (Val-Asn-Gly-Thr-Gln-Ala) were added upstream of the N-terminal of mature interferon; the amount of these proteins was 0.5 to 1 mg per liter of culture. On the other hand, Schein et al. attempted to ligate a DNA fragment coding for mature interferon (IFN) immediately after the region coding for an amino acid of the secretion signal of the alpha-amylase as used by Palva et al. to secrete human IFN protein. However, it has been reported that, in this case, a large amount of an IFN precursor or mature IFN was retained within the cell membrane while the amount secreted into the medium was very little.

Furthermore, the relation between the structure of the cleavage site of a secretion signal and secretion efficiency as well as membrane transport have been discussed (see Reference 21). As a result, it has been determined that in correct cleavage of the cleavage site, the amino acid sequence of the cleavage site plays an important role.

The aforementioned facts suggest that the secretive productivity of a heterologous protein is possibly increased by reproducing an amino acid sequence of an original secretion signal in the junction region between the secretion signal and the heterologous gene product. A possible explanation is that the amino acid sequence of the cleavage site of the original secretion signal can be more easily cleaved by signal peptidase as compared to that of an altered cleavage site. In order to reproduce such a cleavage site of the original secretion signal, two kinds of methods were considered: a method in which the junction region having a nucleotide sequence necessary to reproducing an amino acid sequence of the original secretion signal was inserted between the regions coding for the C-terminal of the secretion signal and the N-terminal of the desired heterologous gene, respectively; and a method in which a DNA sequence coding for the N-terminal region of the heterologous gene was altered so as to reproduce the amino acid sequence of the cleavage site of the original secretion signal.

Also, in the secretion of the HV1-type hirudin, the aforementioned discussion related to the junction of the secretion signal, none of the results have been satisfactory.

In the two methods described above, in the case where an insertion region to reproduce the amino acid sequence of the cleavage site of the original secretion signal is constructed between the C-terminal of the secretion signal and the N-terminal of the HV1-type hirudin, a fusion protein containing extra amino acids at the N-terminal may be secreted (see Reference 14). In particular, it has been pointed out that, in the case of HV1-type hirudin, the presence of such additional amino acids induces a marked decrease in thrombin inhibiting activity as shown in the literature discussed above (see Reference 7).

Furthermore, also in the latter method, it is reported (see Reference 22) that the amino acid sequence of the N-terminal region of the HV1-type hirudin plays an important role in maintaining high thrombin inhibiting activity. It is also reported (see Reference 16) that the amino acid sequence of the N-terminal (residues 1–5) of HV1-type hirudin is related to the configurational maintenance of the C-terminal active site of HV1-type hirudin, the amino acid sequence of the N-terminal region of HV1-type hirudin plays an important role in exerting thrombin inhibiting activity, so that it is quite possible that this alteration causes a decrease in activity. It was difficult in the prior art technique to find out such alteration that high secretion efficiency can be attained without diverse effects on the activity. Furthermore, in this respect, effective alteration of the amino acid sequence has not yet been provided.

SUMMARY OF THE INVENTION

The present inventors have investigated the amino acid sequence of a junction site between a secretion signal and the polypeptide having thrombin inhibiting activity in order to effectively carry out secretion of the polypeptide having thrombin inhibiting activity using the secretion signal without reducing its thrombin inhibiting activity. More specifically, as described later in Comparative Examples 1 and 2, the present inventors have found that the secretion signal of the neutral protease of *Bacillus amyloliquefaciens* is effective for secretory production of HV1-type hirudin. However, in order to attain higher secretion efficiency, investigations have been made on a polypeptide precursor which can increase the yield of secretory production of HV1-type hirudin without diminishing its high thrombin inhibiting activity by modifying the amino acid sequence of the N-terminal region of HV1-type hirudin. As a result, the present inventors have found the structure of a polypeptide in which two amino acid residues in the N-terminal region of the HV1-type hirudin are replaced so as to secrete and produce outside the cells of *Bacillus subtilis* without reducing its high thrombin inhibiting activity, and thus completed the present invention.

This polypeptide has the structure of a so-called precursor before secretion, in which polypeptide having an amino acid sequence wherein the N-terminal region of the HV1-type hirudin is modified as described below is bound immediately after the secretion signal of the neutral protease of *Bacillus amyloliquefaciens*. After removal of the secretion signal in the secreting process, this precursor makes a polypeptide having mature-type thrombin inhibiting activity. This polypeptide can be secreted more efficiently than HV1-type hirudin, and the thrombin inhibiting activity thereof is at the same level as that of HV1-type hirudin.

An object of the present invention is to provide a precursor which can lead to efficient secretion of a polypeptide while maintaining its already high thrombin inhibiting activity.

Another object of the present invention is to provide a secretion vector having a structure for expression of this precursor in a host cell.

Another object of the present invention is to provide a microorganism transformed with this vector, which is suited for efficient secretory production of a polypeptide having thrombin inhibiting activity.

Another object of the present invention is to provide a process for the production of a polypeptide having thrombin inhibiting activity, in which the cells of a transformant are cultivated and a polypeptide having thrombin inhibiting activity is recovered from the culture supernatant.

These objects may be accomplished by replacing valine at the N-terminal and aspartic acid at the fifth residue from the N-terminal of HV1-type hirudin by alanine and glutamic acid, respectively.

As shown in an embodiment of the present invention, a polypeptide having thrombin inhibiting activity at the same level as HV1-type hirudin derived from leeches can now be secreted in a culture supernatant at high efficiency by cultivating transformed cells of *Bacillus subtilis* having an introduced secretion plasmid which is constructed using a promoter, a region coding for a ribosome binding site and a secretion signal coding region all being of a neutral protease gene of *Bacillus amyloliquefaciens*. A polypeptide having thrombin inhibiting activity which can be efficiently secreted in a system having *Bacillus subtilis* as a host has been found, and a method for producing the polypeptide having thrombin inhibiting activity, in which the polypeptide can be recovered and purified from a culture supernatant in a simple manner, is described.

BRIEF DESCRIPTION OF THE DRAWINGS

In these figures, Pm represents a promoter region of the neutral protease gene, SD represents a region coding for a ribosome binding site of the neutral protease gene, pre represents a region coding for a secretion signal of the neutral protease gene, delta-pro represents a 5' region of a propeptide coding region of the neutral protease gene, alpha-amylase represents a DNA sequence coding for a mature alpha-amylase, H represents a DNA sequence coding for a hirudin, delta-H' represents the 5' region of a DNA sequence coding for the modified hirudin, delta-H represents the 5' region of the DNA sequence coding for the hirudin, delta-protease represents the latter half of neutral protease gene, and H" represents a DNA sequence coding for the modified hirudin of the present invention. In FIGS. 1, 3 and 4, A represents adenine, C represents cytosine, G represents cytosine, G represents thymine, and G represents guanine.

DETAILED DESCRIPTION OF THE INVENTION AND PREFERRED EMBODIMENTS

Figure 1:
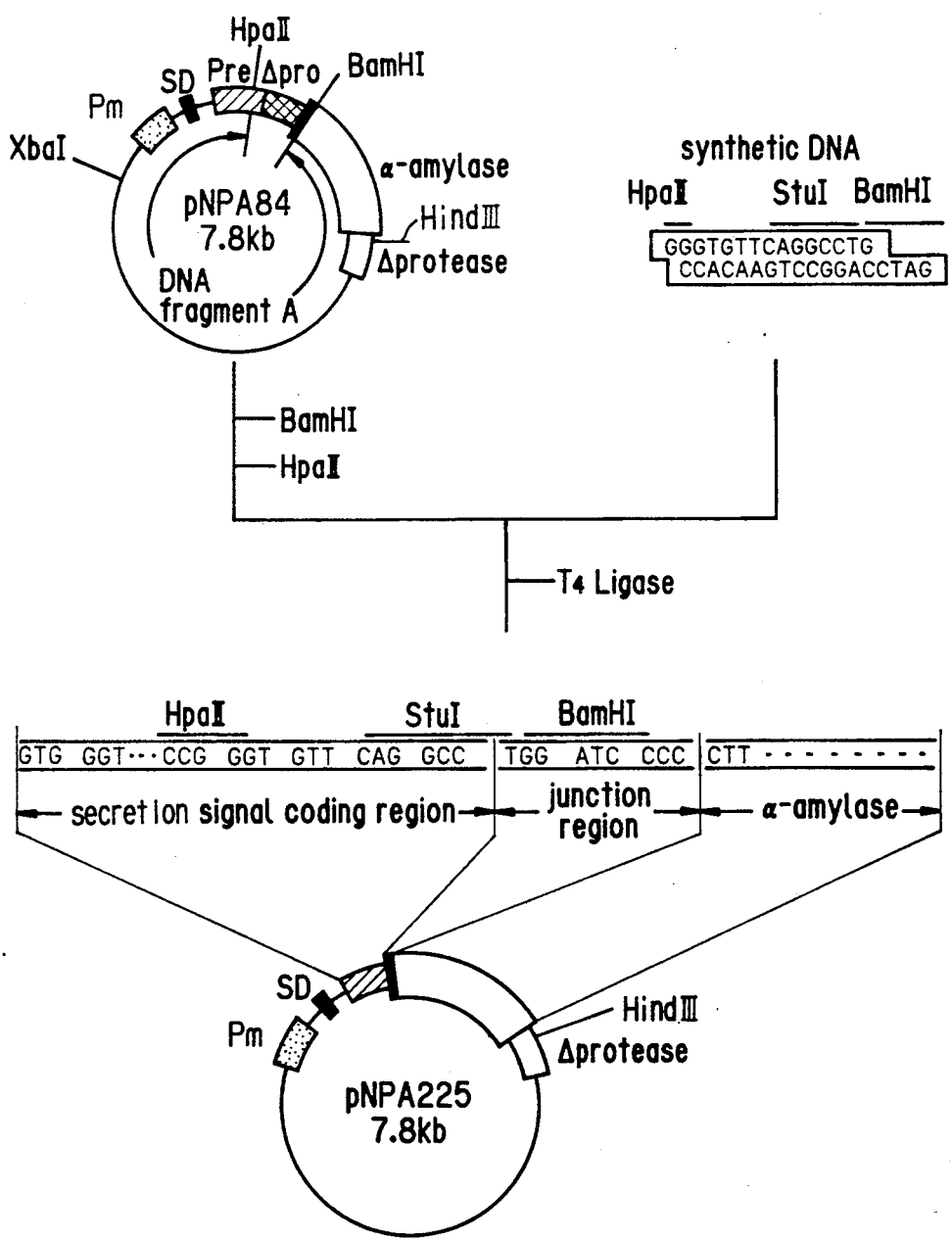
FIG. 1 shows a method of constructing a heterologous protein expression secretion vector, pNPA225.

A polypeptide having high thrombin inhibiting activity according to the present invention has the following amino acid sequence (I) in which valine of the N-terminal end of HV1-type hirudin and aspartic acid at the fifth from the N-terminal end are replaced by alanine and glutamic acid, respectively.

(I):
Ala—Val—Tyr—Thr—Glu—Cys—Thr—Glu—Ser—Gly—Gln—

Asn—Leu—Cys—Leu—Cys—Glu—Gly—Ser—Asn—Val—Cys—

Gly—Gln—Gly—Asn—Lys—Cys—Ile—Leu—Gly—Ser—Asp—

Gly—Glu—Lys—Asn—Gln—Cys—Val—Thr—Gly—Glu—Gly—

Thr—Pro—Lys—Pro—Gln—Ser—His—Asn—Asp—Gly—Asp—

Phe—Glu—Glu—Ile—Pro—Glu—Glu—Tyr—Leu—Gln

A precursor which enables this polypeptide to secrete at high efficiency without reducing its high thrombin inhibiting activity has the following amino acid sequence (II), which is expressed in a host, and the polypeptide having the amino acid sequence (I) can be effectively secreted.

(II):
Met—Gly—Leu—Gly—Lys—Lys—Leu—Ser—Ser—Ala—Val—

Ala—Ala—Ser—Phe—Met—Ser—Leu—Thr—Ile—Ser—Leu—

Pro—Gly—Val—Gln—Ala—Ala—Val—Tyr—Thr—Glu—Cys—

Thr—Glu—Ser—Gly—Gln—Asn—Leu—Cys—Leu—Cys—Glu—

Gly—Ser—Asn—Val—Cys—Gly—Gln—Gly—Asn—Lys—Cys—

Ile—Leu—Gly—Ser—Asp—Gly—Glu—Lys—Asn—Gln—Cys—

Val—Thr—Gly—Glu—Gly—Thr—Pro—Lys—Pro—Gln—Ser—

His—Asn—Asp—Gly—Asp—Phe—Glu—Glu—Ile—Pro—Glu—

Glu—Tyr—Leu—Gln

Expression of this precursor in a host can be carried out by constructing a secretion plasmid having a structure in which a DNA sequence coding for the precursor is functionally ligated downstream the DNA sequences necessary for expression such as a promoter and a region coding for a ribosome binding site (ribosome binding region) so that its expression is possible, and then introducing the secretion vector into a host.

An example of the DNA sequence coding for the amino acid sequence (I) to be used for the construction of the secretion vector is the following DNA sequence (I):

(I):
5' GCCGTTTATACAGAGTGCAC

AGAATCCGGACAAAATTTATGT

TTATGTGAAGAATCTAATGTTT

GTGGACAAGGAAATAAATGTAT

TTTAGGATCTGATGGAGAAAAA

AATCAATGTGTTACAGGAGAAG

GAACACCGAAACCGCAATCTCA

TAATGATGGAGATTTTGAAGAA

ATTCCTGAAGAATATTTACAA 3'

As a DNA sequence coding for the precursor, the following DNA sequence (II) may be used:

(II):
5' GTGGGTTTAGGTAAGAAATT

GTCTAGTGCTGTAGCCGCTTCC

TTTATGAGTTTAACCATCAGTC

TGCCGGGTGTTCAGGCCGCCGT

TTATACAGAGTGCACAGAATCC

GGACAAAATTTATGTTTATGTG

AAGAATCTAATGTTTGTGGACA

AGGAAATAAATGTATTTTAGGA

TCTGATGGAGAAAAAAATCAAT

GTGTTACAGGAGAAGGAACACC

GAAACCGCAATCTCATAATGAT

GGAGATTTTGAAGAAATTCCTG

AAGAATATTTACAA 3'

As the promoter and the ribosome binding region to construct the secretion plasmid, any of those operable in the intended host can be used.

As a structure in which a DNA sequence coding for the precursor is ligated downstream (3' end side) of a DNA sequence containing a promoter and a ribosome binding region, for example, a structure having the following DNA sequence (III) carrying the promoter and the ribosome binding region of the neutral protease gene of *Bacillus amyloliquefaciens* can be used.

(III):
5' GATCTTAACATTTTTCCCCT

ATCATTTTTCCCGTCTTCATTT

GTCATTTTTTCCAGAAAAAATC

GTCATTCGACTCATGTCTAATC

CAACACGTCTCTCTCGGCTTAT

CCCCTGACACCGCCCGCCGACA

GCCCGCATGGACGAATCTATCA

-continued

ATTCAGCCGCGGAGTCTAGTTT

TATATTGCAGAATGCGAGATTG

CTGGTTTATTATAACAATATAA

GTTTTCATTATTTTCAAAAAGG

GGGATTTATTGTGGGTTTAGGT

AAGAAATTGTCTAGTGCTGTAG

CCGCTTCCTTTATGAGTTTAAC

CATCAGTCTGCCGGGTGTTCAG

GCCGCCGTTTATACAGAGTGCA

CAGAATCCGGACAAAATTTATG

TTTATGTGAAGAATCTAATGTT

TGTGGACAAGGAAATAAATGTA

TTTTAGGATCTGATGGAGAAAA

AAATCAATGTGTTACAGGAGAA

GGAACACCGAAACCGCAATCTC

ATAATGATGGAGATTTTGAAGA

AATTCCTGAAGAATATTTACAA

3'

The promoter as used in the present invention means a DNA sequence which RNA polymerase recognizes and binds.

In general, a common DNA sequence is known to be present about 10 nucleotides upstream from the RNA transcriptional origin (referred to as +1). This DNA sequence is 5"TATAAT3' and called "−10 region". Furthermore, another common DNA sequence, 5'TTGACA3', is known to be present about 35 nucleotides upstream from the origin and is called "−35 region". In general, the "−35 region" is considered to be necessary for the recognition of RNA polymerase and the "−10 region" is considered to be necessary for binding of RNA polymerase (see Reference 17).

Bacillus subtilis is known to have several kinds of RNA polymerase. This variety plays an important role in a process of spore formation in Bacillus subtilis, which is associated with a complicated expression regulation. In particular, most of the RNA polymerase in the nutritional growth phase is sigma-55 type RNA polymerase, and thus transcription of most of the genes is known to be carried out with this polymerase (see Reference 18).

The DNA sequence considered to be "−10 region" and "−35 region" of the promoter in the secretion plasmid according to the present invention are, for example, in the DNA sequence (III), 5'TATTAT3' starting from T at the 203th nucleotide from the 5' end and 5'TTGCAG3' starting from T at the 179th nucleotide from the 5' end, respectively. These DNA sequences are highly homologous to the consensus sequences of the −35 and −10 regions which are the recognition sequence and binding sequence of a sigma-55 type RNA polymerase which comprises a major polymerase in the vegetative growth phase of Bacillus subtilis (see Reference 18).

Furthermore, the ribosome binding site is a nucleotide sequence through which mRNA synthesized by RNA polymerase is bound to ribosomes. Generally, ribosome binding region is a DNA sequence commonly observed 5 to 9 nucleotides upstream of an initiation codon and denoted a DNA sequence complementary to the DNA sequence at the 3' end of 16SrRNA. The DNA sequence of 16SrRNA varies depending on the kinds of microorganisms; however, the DNA sequence of 16SrRNA of Bacillus subtilis is known to be 3'UCUUUCCUCC5' (see Reference 18).

A DNA sequence considered to be a ribosome binding region of a secretion plasmid according to the present invention is, for example, in the DNA sequence (III), 5'AAAGGGGG3' starting from A at the 236th nucleotide from the 5' end. This DNA sequence is extremely highly complementary to 16SrRNA of Bacillus subtilis.

The promoter and the ribosome binding region play important roles in the expression of the gene. Furthermore, it is widely known today that these DNA sequences are related to the expression efficiency of the gene (see Reference 18).

Where the gene of a desired protein is expressed using a Bacillus as a host, RNA polymerase and a ribosome of the bacteria of the genus Bacillus are restrictively specific to the promoter and ribosome binding site (see Reference 18), so that these regions are preferably those derived from bacteria of the genus Bacillus (see Reference 19).

A secretory protein is synthesized in a cell as a precursor protein in a form in which a secretion signal is added upstream of the N-terminal end of its mature protein; however, the secretion signal is removed in the process of secretion and thus the precursor is secreted outside the cell as the mature protein (see Reference 20). A mature protein as used herein means a protein in which its own secretion signal is removed from the secretory protein. Furthermore, a secretion signal denotes a polypeptide consisting of 20 to 30 amino acid residues which is present upstream of the N-terminal end of the mature protein. The secretion signal has the following characteristics. The presence of basic amino acids near the end of the N-terminal, the presence of a cluster of hydrophobic amino acids in the center, and the presence of amino acids having small side chains at the cleavage site of the secretion signal are known. This polypeptide will be removed in the course of secretion and is considered to play an important role in passing of a precursor protein through a cytoplasmic membrane (see Reference 20).

The amino acid sequence of the secretion signal of neutral protease of Bacillus amyloliquefaciens used in the construction of a secretion plasmid according to the present invention is Met-Gly-Leu-Gly-Lys-Lys-Leu-Ser-Ser-Ala-Val-Ala-Ala-Ser-Phe-Met-Ser-Leu-Thr-Ile-Ser-Leu-Pro-Gly-Val-Gln-Ala-. It has a typical secretion signal construction and comprises the amino acid sequence of 1 to 27 of the amino acid sequence (II).

As a DNA sequence coding for this secretion signal, for example, as the DNA sequence (III), the following sequence

5' GTGGGTTTAGGTAAGAAATTGTCTAGTGCTGTAGCCGCTTCC

-continued
TTTATGAGTTTAACCATCAGTCTGCCGGGTGTTCAGGCCGCC 3' starting from G at the 251th nucleotide from the 5' end can be used.

The inventors have constructed an HV1-type hirudin secretion plasmid by ligating a DNA fragment coding for HV1-type hirudin immediately after the promoter and the ribosome binding region of the neutral protease gene of *Bacillus amyloliquefaciens* and the secretion signal coding region of the neutral protease gene, as described in Comparative Example 1. Furthermore, as shown in Comparative Example 2, the present inventors have succeeded in secreting HV1-type hirudin in an amount of 80 to 100 mg per liter of culture fluid in the culture supenatant by cultivating transformants obtained by transformation of *Bacillus subtilis* with this plasmid. However, in this case, the presence of contaminated inactive hirudin lacking thrombin inhibiting activity was revealed due to the S-S bonds are not cross-linked accurately, though only in a small quantity.

As described above, since such inactive hirudin is synthesized even in the case where HV1-type hirudin is produced intracellularly in *E. coli*, one of the possible reasons for the production of inactive hirudin is poor efficiency of secretion also in the case where *Bacillus subtilis* is used as a host. It is believed that because of the decrease in efficiency of hirudin secretion, inactive hirudin is formed.

Consequently, in order to solve this problem, to reduce the rate of contamination of incorrectly bridged S-S bindings, the present inventors modified the amino acid sequence of the junction region between the secretion signal and the mature hirudin.

As described above, Palva et al. (see Reference 14) and Schien et al. (see Reference 15) have reported that alteration of the original amino acid sequence of the secretion signal to other amino acid sequences due to junction between the secretion signal and a heterologous protein, effects the efficiency of secretive production of the heterologous protein.

Palva et al. have bound the DNA fragment coding for mature interferon (IFN) immediately after the region encoding Ala-Val containing a cleavage site of the secretion signal of the alpha-amylase of *Bacillus amyloliquefaciens*, or via a junction region consisting of 5 amino acid residues (Asn-Gly-Thr-Glu-Ala) and attempted the secretion of the human IFN. It was reported that, in this case, the secretion signal was removed and the secreted interferon was a fusion protein which was secreted and accumulated in a form in which one amino acid (Val) or 6 amino acids (Val-Asn-Gly-Thr-Gln-Ala) were added upstream of the N-terminal of the mature interferon; the amount of these proteins were 0.5 to 1 mg per liter of culture. On the other hand, Schein et al. attempted to ligate the DNA fragment coding for mature interferon (IFN) immediately after the region encoding Ala as the C-terminal of the secretion signal of the alphaamylase used by Palva et al. to secrete human IFN. In this case, however, it has been reported that a great amount of a precursor IFN or the mature IFN remains in the cells of the bacteria and the efficiency of the secretion into a culture medium is very low.

Furthermore, the relationship between the structure of the cleavage site of the secretion signal and secretion efficiency and membrane transport have been discussed (see Reference 21). As a result, it has been revealed that for the correct cleavage of the cleavage site, the amino acid sequence of the cleavage site plays an important role.

These facts suggest that the secretory productivity of a heterologous protein is possibly increased by reproducing the amino acid sequence of the original secretion signal in the junction between the secretion signal and the heterologous gene product. A possible explanation is that the amino acid sequence of the cleavage site of the original secretion signal can be more easily cleaved by signal peptidase as compared to that of the altered cleavage site. In order to reproduce such a cleavage site of the original secretion signal sequence, two methods were considered: one in which a junction having a nucleotide sequence necessary to reproduce an amino acid sequence of an original secretion signal was inserted between the regions encoding the C-terminal of the secretion signal and the N-terminal of a desired heterologous respectively, or a method in which the DNA sequence coding for the N-terminal region of HV1-type hirudin was altered to alanine to reproduce alanyl-alanine in the cleavage site of the original secretion signal.

Where an insertion region to reproduce the amino acid sequence of the cleavage site of the original secretion signal is constructed between the C-terminal of the secretion signal and the N-terminal of the HV1-type hirudin, a fusion protein having extra amino acids at the N-terminal may be secreted (see Reference 14). In particular, it has been pointed out that, in the case of HV1-type hirudin, the presence of such an additional amino acids induces a marked decrease in thrombin inhibiting activity as shown in the aforementioned literature (see Reference 7).

Also in the method of replacement of the amino acid sequence of the N-terminal region of the HV1-type hirudin, as appeared in the report (see Reference 22) to play an important role in maintaining its high thrombin inhibiting activity, such modification is a difficult problem. After intensive investigations, the inventors have reached a solution to this problem.

The inventors have noticed that the plasmid for secretion of HV1-type hirudin in Reference Example 1 provided the cleavage site of the secretion signal consisting of alanyl-valine, where the amino acid at the C-terminal end of the secretion signal is attached to the amino acid at the N-terminal end of the HV1-type hirudin, and that the amino acid sequence of the cleavage site differs from original alanyl-alanine in the neutral protease.

On the other hand, the mechanism of expression of thrombin inhibiting activity of the HV1-type hirudin has already been investigated. According to the investigation, it is considered that the C-terminal of the HV1-type hirudin (residues 56 to 65) is bound to thrombin and then the three-dimensional structure of thrombin is greatly changed, which results in the expression of thrombin inhibiting activity (see Reference 23).

Furthermore, as has already been reported, the amino acid sequence of the N-terminal (residues 1 to 5) of HV1-type hirudin is considered to be an important sequence since it is related to the maintenance of the structure of the C-terminal active site of the HV1-type hirudin (see Reference 16).

From these facts, it is easily determined that in the case where the original cleavage site for signal peptidase is established in the junction by replacing the N-terminal region of HV1-type hirudin, even if the polypeptide, in which the N-terminal region of HV1-type hirudin is replaced, is effectively secreted in the culture, the secreted polypeptide is likely to have only weak thrombin inhibiting activity.

Using recombinant DNA techniques, a system for free creation of proteins which undergo artificial mutations is recently available. As a result, a science called "protein engineering" providing the creation of proteins more active, more stable or having entirely new functions is about to be established. However, in fact, there is no principle that could make a guiding principle for modification of proteins, and consequently, pertinent modification of proteins cannot yet be carried out. Today, there is no guiding principle regarding the methods for the modification not to lower thrombin activity when the cleavage site of the original secretion signal is reproduced by replacement of the N-terminal region of hirudin as described above.

The present inventors have attempted the replacement of the amino acid residues, from the 1st to 5th, of the N-terminal end of HV1-type hirudin, which is thought to be important in the expression of thrombin inhibiting activity in order to minimize the effect of alteration of the N-terminal amino acid of the HV1-type hirudin to valine. They have found that a polypeptide in which valine at the N-terminal end and aspartic acid at the 5th from the N-terminal end are replaced by alanine and glutamic acid, respectively, guarantees excellent secretion efficiency and high thrombin inhibiting activity. As shown in Examples 1 and 2, it has been found that a novel polypeptide, which has high thrombin inhibiting activity and is not present in nature, can be secreted and efficiently produced in a system using *Bacillus subtilis* as a host.

As described above, the polypeptide of the present invention having thrombin inhibiting activity has the amino acid sequence (I).

Also described is a precursor of the polypeptide, having thrombin inhibiting activity, as used in the present invention which has the amino acid sequence (II) and is a polypeptide in which a polypeptide having thrombin inhibiting activity is attached immediately after the C-terminal end of the secretion signal of neutral protease of *Bacillus amyloliquefaciens*. A DNA sequence coding for this polypeptide can be obtained by ligating codons corresponding to individual amino acid residues. In general, since two or more codons code for one amino acid, in the construction of the secretion plasmid of the present invention, several kinds of DNA sequences coding for the polypeptide having thrombin inhibiting activity are present. Among them, the present inventors have preferably used the DNA sequence (II).

This DNA sequence (II) can be easily obtained by assembling chemically synthesized fragments. The following points were regarded to select the DNA sequence (II) among many DNA sequences which code the common amino acid sequence:

Recently, DNA sequences of a variety of genes have been revealed, so it has become possible to determine the frequency of the use of codons in the genes. As a result, it was observed that the frequency of the codon usage differs from organism to organism. The frequency of the codons is thus tailored to that of the intended host. Consequently, DNA sequences are generally designed so as to contain many codons which are appropriate to that organism to be used as a host when a DNA sequence is chemically synthesized for efficient expression. In the present invention, in particular, on the supposition that the expression is carried out using *Bacillus subtilis* as a host, a DNA sequence which is designed to contain many codons appropriate to *Bacillus subtilis* was utilized.

The inventors have discovered a recombinant DNA, i.e. a secretion plasmid, capable of secreting a large amount of the HV1-type hirudin as described in Examples 1 and 2, which recombinant DNA was constructed using the neutral protease gene of *B. amyloliquefaciens* so as to ligate a gene coding for the HV1-type hirudin to the secretion signal coding region of the neutral protease gene.

As a vector DNA to construct the secretion plasmid in this case, any replicable DNA derived from bacteria of the genus Bacillus can be used. Examples generally used are those derived from Staphylococcus, such as plasmids pUB110, pTP5, pC194, pDB9, pBD64, pC16, pE194 and their derivatives. All the strains of *Bacillus subtilis* carrying the above-mentioned plasmids have been deposited at the Bacillus Stock Center in Ohio University (484 West 12th Avenue, Columbus Ohio 43210 USA) and are available to the public.

In particular, as a vector DNA to be used in the present invention, any replicable plasmid derived from bacteria of the genus Bacillus may be used; however, pUB110 is advantageously used because of the through knowledges of its molecular biology and this vector is maintained stably in bacteria of the genus Bacillus.

As will be described in the following Examples, a vector for expression and secretion of a heterologous protein was used to construct the secretion plasmid of the present invention.

This vector comprised:
(a) a DNA fragment replicable in *B. subtilis*;
(b) a DNA fragment comprising, from 5' to 3', a promoter region, a ribosome binding region and a secretion signal coding region, all regions being of neutral protease of *B. amyloliquefaciens*; and
(c) a site through which a gene coding for a heterologous protein can be inserted and ligated to the DNA fragment (b) downstream the secretion signal coding region so as to express and secrete the heterologous protein.

Thus, a gene coding for a polypeptide having thrombin inhibiting activity was inserted into the vector through the site (c) to obtain the secretion plasmid of the present invention useful for highly efficient secretion of the polypeptide having thrombin inhibiting activity. As a result, the polypeptide encoded by this secretion plasmid was a precursor-type polypeptide having the amino acid sequence (II) in a form in which an amino acid sequence consisting of 27 amino acid residues was added upstream of the N-terminal of the polypeptide bearing thrombin inhibiting activity.

Construction of the secretion plasmid according to the present invention can be easily performed by ligating a chemically synthesized DNA fragment containing the DNA sequence (III) to a replicable vector DNA fragment derived from bacteria of Bacillus, which is cleaved with an appropriate restriction endonuclease. In this case, the two DNA fragments can be ligated, for example, via common restriction sites, and/or using a synthetic DNA linker and/or by ligating to the blunt end.

Using the secretion plasmid of the present invention, *Bacillus subtilis* can be transformed so as to obtain transformants.

The *Bacillus subtilis* may be transformed using any convenient method. For example, the method of Chang et al. (see Reference 24) can be used. This method can be divided into three steps.
1. Cell wall-free *Bacillus subtilis*, namely protoplasts, are made by treating *Bacillus subtilis* in an isotonic solution.
2. The protoplasts are transformed with the secretion plasmid using a polyethylene glycol solution.
3. The cell walls of the protoplasts are reproduced in a reproductive culture medium and transformed cells of *Bacillus subtilis* are selected.

In order to obtain a polypeptide having thrombin inhibiting activity using the transformed strain, cells of the strain may be cultured in a liquid medium by an ordinary method. For example, there is a method in which cells of the transformant strain are inoculated in 400 ml of an LB medium (see Reference 25) in a 2-liter volume of Erlenmeyer flask and then incubated at 37° C. for about 20 hours with shaking, preferably until a polypeptide having thrombin inhibiting activity is produced and secreted in maximum yield.

The transformants of the present invention are cultivated in a liquid medium containing a utilizable carbon source, a nitrogen source and an inorganic salt source. For example, a commonly used liquid medium in general is the LB medium.

As a host bacterial strain, any suitable bacterial strains of the genus Bacillus which are transformed by the secretion plasmid of the present invention can be used. However, strains of *Bacillus subtilis* species are preferably used because of the available knowledge of this species in terms of genetics, biochemistry, molecular biology and applied microbiology, and their great safety.

Preparation of the polypeptide having thrombin inhibiting activity from a culture fluid is possible by recovering and purifying processes using the culture supernatant. The present inventors have found that, after adjustment of the pH of this culture supernatant to 3 with hydrochloric acid, the polypeptide having thrombin inhibiting activity remains in the supernatant fraction obtained by treating at 70° C. for 15 minutes and centrifuging to remove the resulting proteinous precipitate. The yield was increased to 23% of the total protein and thus the rate of foreign protein contamination was extremely low. Consequently, the polypeptide having thrombin inhibiting activity secreted in the culture can be easily purified from this supernatant using cation exchange chromatography, anion exchange chromatography and inverse-phase chromatography.

The present inventors found that the polypeptide having thrombin inhibiting activity corresponding to 10 mg/l.A660 was secreted and accumulated by culturing transformants obtained by transformation of *Bacillus subtilis* with the HV1-type hirudin secretion plasmid shown in Comparative Example 1 under the conditions shown in Comparative Example 2. The present inventors found that by culturing cells of *Bacillus subtilis* transformed with the secretion plasmid which was constructed by modifying the HV1-type hirudin secretion plasmid as shown in Example 1 of the present invention, under the conditions shown in Example 2, a polypeptide having thrombin inhibiting activity corresponding to 18 mg/l.A660 was more efficiently secreted and accumulated than as compared to that in Comparative Example 2. Further, the optical density unit (A660) of the culture, which indicates the extent of the growth of *Bacillus subtilis* herein, was 10 in all cases. This unit (mg/l.A660) is the value obtained by dividing the amount of polypeptide (mg) having thrombin inhibiting activity accumulated in the culture supernatant (1 l) by the optical density (A660) indicating the growth of *Bacillus subtilis* in the culture.

It was determined that, after adjustment of the pH to 3, of the culture supernatant (1 liter) prepared in Example 2 to 3 with hydrochloric acid, 70 mg of the polypeptide having thrombin inhibiting activity could be obtained from the supernatant fraction obtained by treating at 70° C. for 15 minutes and centrifuging to remove the resulting proteinous precipitate, followed by purification using cation exchange chromatography, anion exchange chromatography and inverse-phase chromatography.

The secretion plasmid of the present invention has a DNA region, in which the 5' end of a gene coding for the modified hirudin is directly ligated immediately after the 3' end of the secretion signal coding region from the neutral protease gene of *B. amyloliquefaciens*. The modified hirudin has alanine at the N-terminal and aspartic acid at the 5th residue in place of valine and glutamic acid in the wild-type hirudin, respectively, as described above.

Therefore, a polypeptide as the precursor comprising the secretion signal and the modified hirudin, in which the C-terminal of the secretion signal and the N-terminal of the modified hirudin are bound, is considered to be synthesized in the cell or on the cell membrane of the transformant carrying the secretion plasmid of the present invention.

Generally, it is known that a secretion signal is removed in the process of secretion. However, Schein et al. (see Reference 15) have reported that simply by ligating a DNA fragment coding for a heterologous protein immediately after a DNA fragment comprising a promoter, a ribosome binding region and a region coding for the secretion signal, all being of a gene coding for a secretory protein, the heterologous protein in which the secretion signal is removed from a precursor protein carrying the heterologous protein attached downstream of the secretion signal is considered to be synthesized in the cell (see Reference 15). Furthermore, their reports are not sufficiently instructive to develop a method for the effective secretion of a heterologous protein. Also in the present invention, it was not clear whether the modified hirudin, from which the secretion signal is removed, is secreted through a precursor polypeptide in which the N-terminal of the modified hirudin having the amino acid sequence (I) is attached immediately after an amino acid at the C-terminal of secretion signal of neutral protease of *B. amyloliquefaciens*. Moreover, as already mentioned, the amino acid sequence (positions 1 to 5) in the N-terminal region of hirudin plays an important role in maintaining a structure of a sequence relating to the expression of thrombin inhibiting activity so that it is highly probable that even if a polypeptide which was constructed by replacing amino acids in this N-terminal region was well secreted, the thrombin inhibiting activity was lowered.

The present inventors have found that, as shown in the Examples of the present invention, as a result of replacement of an amino acid in the N-terminal of HV1-type hirudin, surprisingly, a polypeptide having thrombin inhibiting activity at the same level as the original HV1-type hirudin is secreted more efficiently than the original HV1-type hirudin.

The present invention is based on the results of the research of the Research and Development Project of Basic Technology for Future Industries of the New Energy and Industrial Technology Development Organization.

The present invention will be illustrated by the following Examples: however, these examples are not to be construed to limit the scope of the present invention.

PRODUCTION EXAMPLE 1

Construction of vector pNPA225 for expression and secretion of a heterologous protein Vector pNPA225 for expression and secretion of a heterologous protein was constructed by the method illustrated in FIG. 1. This vector had a DNA fragment comprising, 5' to 3', a promoter region, a ribosome binding region and a secretion signal coding region, all regions being of neutral protease gene of *B. amyloliquefaciens* and a structure for inserting a gene for the heterologous protein immediately downstream the secretion signal coding region.

Plasmid pNPA84 as the starting material had a structure in which a DNA fragment comprising a promoter region, a ribosome binding region, a secretion signal coding region and a 5' region of a pro-peptide coding region (a truncated pro-peptide coding region), all regions being of the neutral protease gene; and a gene coding for a mature alpha-amylase represented by "alpha-amylase" in the Figures, which was operably ligated to the 5' region of the pro-peptide coding region, were inserted into pUB110 capable of replication in *B. subtilis* and expression of kanamycin resistance.

The mature alpha-amylase gene denotes a DNA fragment coding for a protein having alpha-amylase activity, starting with leucine, present in nature. From the cells of the transformed strain MT8400 (FERM BP-923) carrying this plasmid pNPA84, pNPA84 was prepared according to the method of Tabak et al. (see Reference 26). This pNPA84 DNA was digested with the restriction endonuclease HpaII (a product of Takara Shuzo K. K.) and BamHI (a product of Takara Shuzo K. K.), and the resultant DNA fragment of about 7.8 Kb (hereinafter referred to as DNA fragment A) was purified by electrophoresis using agarose gel. This DNA fragment A contained the promoter region, the ribosome binding region and the region coding for the secretion signal lacking the C-terminal region.

Separately, in order to create a cleavage site for the restriction endonuclease StuI at the 3' end of the secretion signal coding region of the neutral protease gene, two kinds, 15 mer and 18 mer, of synthesized oligonucleotides (5'GGGTGTTCAGGCCTG3' and 5'GATC-CAGGCCTGAACACC3') were synthesized by the improved triester method (see Reference 27). One microgram each of the two kinds of synthesized oligonucleotides were phosphorylated using T4 polynucleotide kinase (a product of Takara Shuzo K. K.) and dATP (a product of Pharmacia Co.) (see Reference 28). Subsequently, these reaction products were mixed, heated in hot water for 3 minutes and then gently cooled so as to anneal the two kinds of synthesized oligonucleotides. Then, the DNA fragment A (0.5 microgram) and the annealed synthesized oligonucleotide (1 microgram) were ligated using T4 ligase (a product of Takara Shuzo K. K.) to obtain the vector pNPA225.

COMPARATIVE EXAMPLE 1

Construction of the HV1-type hirudin secreting plasmid pNPH208

Figure 2:
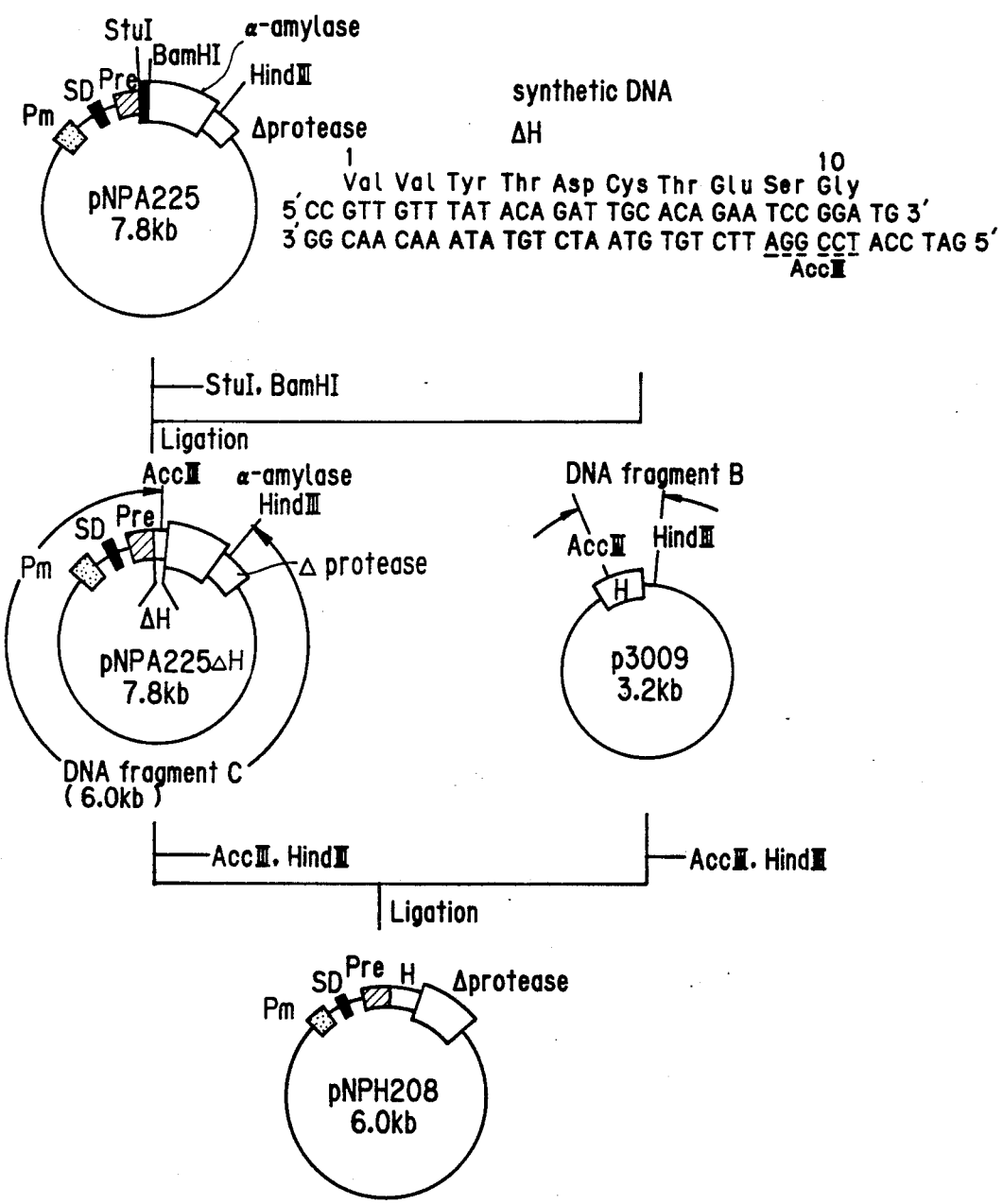
FIG. 2 shows a method of constructing a HV1-type hirudin secreting plasmid, pHPH208.

Plasmid pNPH208 was constructed according to the method illustrated in FIG. 2.

First, in order to construct a DNA fragment containing a DNA region coding for the amino acid from the N-terminal end to the 10th residue of the HV1-type hirudin, two kinds of oligonucleotides (5'CCGTTGTTTATACAGATTGCACAGAATCC-GGATG3' and 5'GATCCATCCGGATTCTGT-GTAATCTGTATAAACAACGG3') were synthesized according to a conventional method.

Then, one microgram each of the synthesized oligonucleotides obtained was annealed after phospholylation. This was ligated to the pNPA225 DNA (0.5 microgram) cleaved with the restriction endonuclease StuI and BamHI, using T4 ligase (a product of Takara Shuzo K. K.). Thus, the hybrid plasmid pNPA225 delta-H in which a DNA fragment coding for the N-terminal region of the HV1-type hirudin (corresponding to the region from the N-terminal end to the 10th amino acid residue) immediately after the region coding for the secretion signal of the neutral protease.

Figure 3:
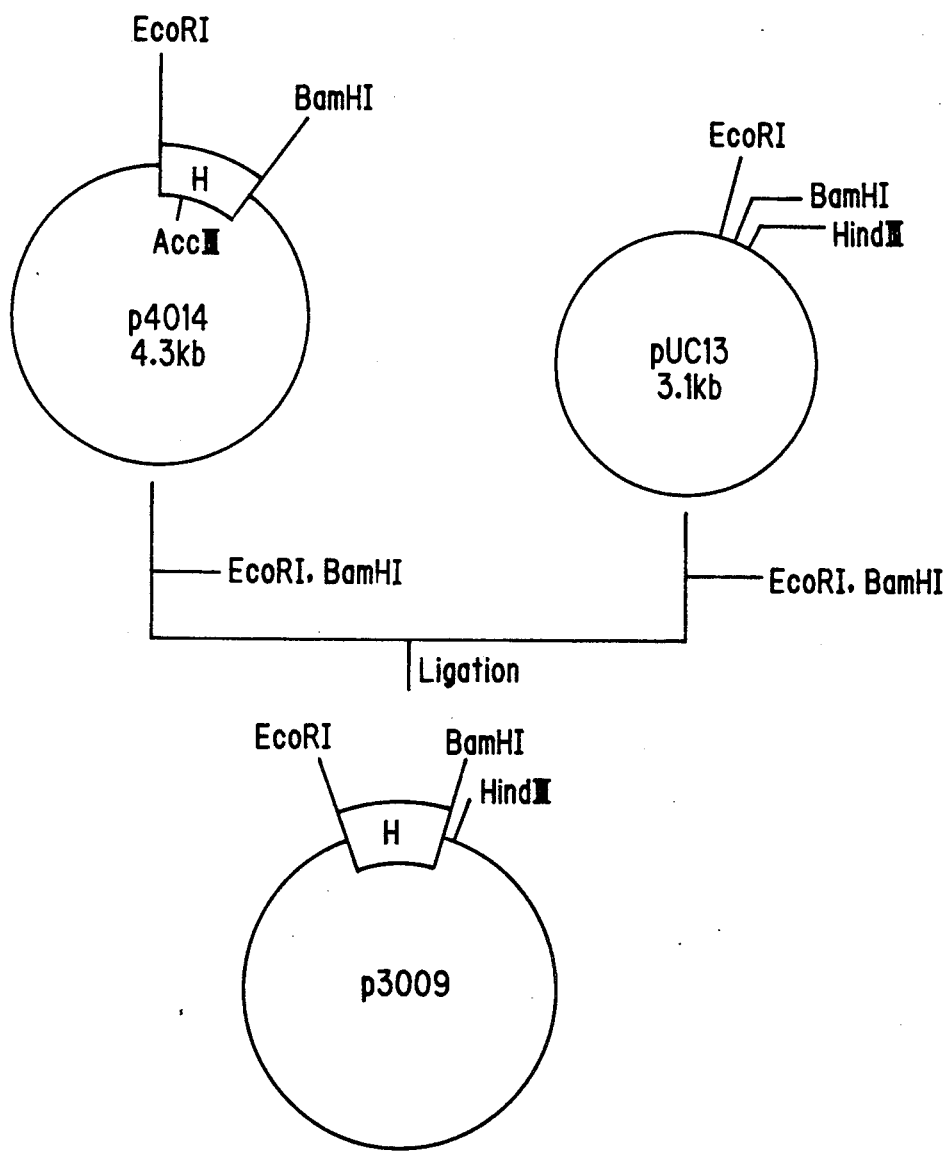
FIG. 3 shows a method of constructing a hybrid plasmid p3009 containing a DNA sequence coding for hirudin.

The strain MTE4014 (FERM BP-1985) transformed by plasmid p4014 constructed from a synthesized DNA which was chemically synthesized by selecting codons frequently used, namely the most appropriate codons (see Reference 29) and the vector pBR322 DNA has already deposited. A fragment coding for the HV1-type hirudin was obtained from the transformed strain p4014 as follows: First, p4014 was cleaved with the restriction endonucleases EcoRI and BamHI and thus a DNA fragment containing the HV1-type hirudin was obtained. This DNA fragment was inserted and ligated between the cleavage sites of the restriction endonucleases EcoRI and BamHI of plasmid pUC13 to construct the hybrid plasmid p3009 (FIG. 3). This p3009 DNA (2 micrograms) was digested with the restriction endonucleases AccIII and HindIII and then a DNA fragment (DNA fragment B) containing a DNA region coding for the amino acid sequence of the 11th to the C terminal end of the HV1-type hirudin was purified using preparative agarose gel electrophoresis. This DNA fragment (1 microgram) and a DNA fragment of about 6.0 Kb obtained by digesting pNPA225 delta-H with the restriction endonucleases AccIII and HindIII (DNA fragment C) (1 microgram) were ligated using T4 ligase and thus the HV1-type hirudin secreting plasmid pNPH208 was constructed. This pNPH208 was a hybrid plasmid containing a structure in which a DNA fragment coding for the mature HV1-type hirudin was ligated immediately after the promoter region, the ribosome binding region and the region coding for the secretion signal, all regions being of the neutral protease gene of *Bacillus amyloliquefaciens*.

COMPARATIVE EXAMPLE 2

Secretive production of HV1-type hirudin by HV1-type hirudin secreting plasmid

The cells of *Bacillus subtilis* MT-430 strain (FERM BP-1079) were transformed with plasmid pNPH208 constructed in Comparative Example 1 by the method of Chang et al. (see Reference 24). The resultant transformant MT-208 (FERM BP-1983) was cultured using a 2-fold concentrated LB medium and incubated at 37° C. for 20 hours with shaking. The thrombin inhibiting activity of the resultant culture supernatant was measured. The thrombin inhibiting activity was determined by measuring the rate of inhibition against thrombin in hydrolysis activity using a synthetic substrate, H-D-phenylanyl-L-pipecolyl-L-arginyl-p-nitroanilide (see Reference 30). Namely, 50 microliters of a thrombin (a product of Mochida Seiyaku Co., Ltd.) solution (20 IU/ml) and 50 microliters of a buffer solution (50 mM Tris-HCl, pH 8.0) were mixed under a neutral to acid condition and incubated at room temperature for 2 minutes, and then 50 microliters of the mixture was added to an H-D-phenylanyl-L-pipecolyl-L-arginyl-p-nitroanilide (a product of Daiichi Kagaku Yakuhin Co., Ltd.) solution (final substrate concentration: 0.25 mM). After the reaction was started, release of p-nitroanilide was measured at a wave length of 405 nm and the increase in the absorption per unit of time was referred to as a.

Subsequently, a sample solution was added in place of the buffer solution and the increase in the absorption at a wave length of 405 nm was measured in the same manner and this measurement was referred to as b. By calculating (a-b)/a, the thrombin inhibiting activity of the culture supernatant was determined. One unit of the thrombin inhibiting activity was identified as the amount which neutralizes 1 NIH unit of thrombin.

In the supernatant obtained by culturing at 37° C. for 20 hours using a 20-fold concentrated LB medium, HV1-hirudin having an activity sufficient to inhibit 80 to 100 mg thrombin per 1 liter medium was accumulated. The optical density (A 660), indicating the growth rate of Bacillus subtilis herein, was 10.

An SDS-PAGE analysis of the precipitate obtained by adding trichloroacetic acid to the supernatant showed that a large amount of protein having the same size as a hirudin standard obtained by purifying the HV1-type hirudin purchased from Sigma was accumulated in the culture supernatant. Gel-scanner densitometer analysis of this protein showed that the amount of the HV1-type hirudin present in the culture supernatant of MT-208 strain was as much as 5%. Thrombin inhibiting activity was retained in the supernatant fraction obtained by treating at 70° C. for 15 minutes and centrifuging to remove the resulting proteinous precipitate, and furthermore, the yield of the HV1-type hirudin was increased to 20% of the total protein in the supernatant fraction. Thus, the rate of foreign protein contamination was extremely low. The HV1-type hirudin was purified from this supernatant fraction using DEAE-Sepharose column chromatography and CM-Sepharose column chromatography. Specifically, the supernatant fraction obtained by treating the culture supernatant by heat at 70° C. for 15 minutes was added to a DEAE-Sepharose column washed with a 20 mM Tris-HCl buffer solution (pH 8.0), and then eluted using a concentration gradient of 0 to 0.5M NaCl. The resultant fractions having thrombin inhibiting activity were collected, dialyzed against a 20 mM sodium acetate-HCl buffer solution (pH 3.0), and then added to a CM-Sepharose column washed with a 20 mM sodium acetate-HCl buffer solution (pH 3.0). The elution was carried out by using a concentration gradient of 0 to 0.2M NaCl. Eluted fractions having thrombin inhibiting activity were collected and subjected to inverse-phase chromatography using a Synchropack RP8 (a product of SynChrom, Inc.) column and fractions having thrombin activity and a small number of fractions having no thrombin inhibiting activity were recovered.

Analysis of polypeptides contained in these fractions using SDS-PAGE revealed that the polypeptides appeared as a single band on SDS-PAGE and, in addition, had the same molecular weight as the HV1-type hirudin standard obtained by purifying leech-origin HV1-type hirudin purchased from Sigma. Using these proteins, the N-terminal amino acid sequences were determined (see Reference 31). The sequence for both proteins was Val-Val-Tyr-Thr-Asp which was identical with the N-terminal amino acid sequence of the HV1-type hirudin derived from leeches.

These results showed that the polypeptide having the same molecular weight as the HV1-type hirudin, which was produced and secreted by the Bacillus subtilis strain transformed with the HV1-type hirudin secreting plasmid, was secreted in a form in which the secretion signal peptide was correctly removed. The thrombin inhibition experiment revealed that the polypeptide having thrombin inhibiting activity reacted stoichometrically with thrombin at a ratio of 1:1.14.

These facts showed that the polypeptide having thrombin inhibiting activity, which is produced and secreted by the Bacillus subtilis strain transformed with the HV1-type hirudin secretion plasmid, has the same hirudin inhibiting activity as the HV1-type hirudin derived from leeches. On the other hand, an inactive-type polypeptide having no thrombin inhibiting activity in spite of having the same structure as the HV1-type hirudin, is considered as a polypeptide in which S-S bonds necessary for expression of thrombin inhibiting activity are not correctly bridged.

EXAMPLE 1

Construction of secretion plasmid pNPH141

Figure 4:
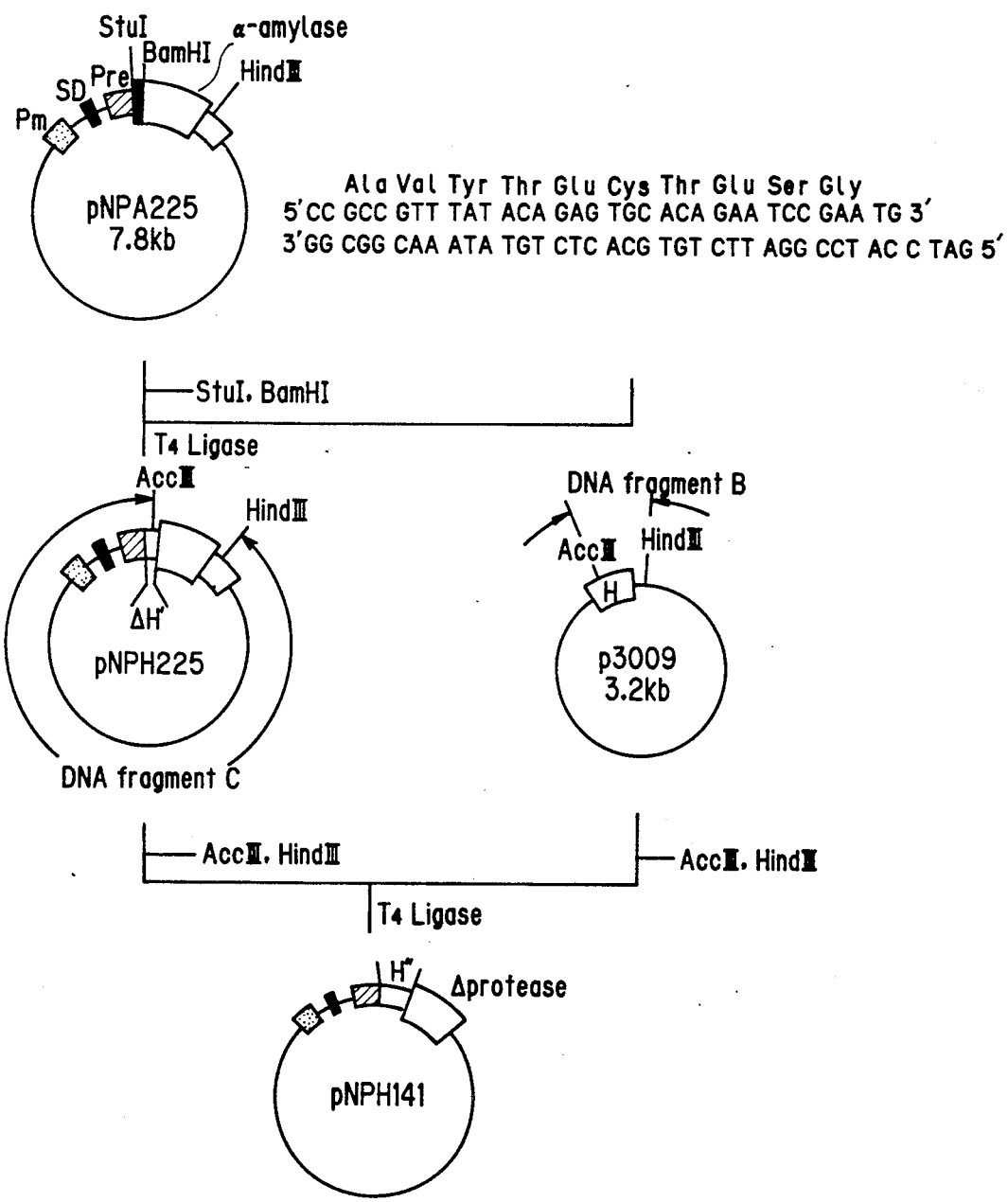
FIG. 4 shows a method of constructing a hirudin secreting plasmid, pNPH141.

Plasmid pNPH141 was constructed according to the method illustrated in FIG. 4.

First, in order to construct a DNA fragment containing a DNA region coding for amino acids from the N-terminal end to the 10th residue of a polypeptide, in which the N-terminal valine and aspartic acid at the 5th residue from the N-terminal of the HV1-type hirudin were replaced by alanine and glutamic acid, respectively, two kinds of oligonucleotides (5'CCGCCGTTTATACAGAGT-GCACAGAATCCGGATG3' and 5'GATCCATCC-GGATTCTGTGCACTCTGTATAAACGGCGG3') were synthesized according to a conventional method. Then, 1 microgram each of the synthesized oligonucleotides obtained was annealed after phospholylation. This was ligated to the pNPA225 DNA (0.5 microgram) cleaved with the restriction endonucleases StuI and BamHI using T4 ligase (a product of Takara Shuzo K.K.) to obtain the hybrid plasmid pNPA225. This plasmid had a structure in which a DNA fragment coding for a 10 amino acid residue-polypeptide, which corresponded to the N-terminal region of the modified HV1-type hirudin having alanine at the N-terminal and glutamic acid at the 5th residue from the N-terminal in place of valine and aspartic acid of the wild type of the HV1-type hirudin, was ligated immediately downstream the region coding for the secretion signal peptide from the neutral protease gene.

A DNA fragment coding for the HV1-type hirudin was prepared using the transformed strain p4014 according to the method shown in Comparative Example 1. Namely, p4014 was cleaved with the restriction endonucleases EcoRI and BamHI and thus a DNA fragment coding for the hirudin was prepared. This DNA fragment was inserted and ligated between the cleavage sites of the restriction endonucleases EcoRI and BamHI of plasmid pUC13 plasmid to construct the hybrid plasmid p3009. This p3009 DNA (2 micrograms) was digested with the restriction endonucleases AccIII and HindIII and then a DNA fragment (DNA fragment B) containing a DNA region coding for the amino acid sequence of the 11th to the C terminal end of the HV1-type hirudin was purified using preparative agarose gel electrophoresis. This DNA fragment (1 microgram) and a DNA fragment of about 6.0 Kb obtained by digesting pNPA225 with the restriction endonucleases AccIII and HindIII (DNA fragment C) (1 microgram) were ligated using T4 ligase and thus the secretion plasmid pNPH141 of the present invention was constructed. This pNPH141 is a hybrid plasmid carrying a fused DNA sequence in which a gene coding for the polypeptide as the modified HV1-type hirudin, which had alanine at the N-terminal end and glutamic acid at the 5th residue from the N-terminal in place of valine and aspartic acid, respectively, was ligated immediately downstream a part comprising the promoter region, the ribosome binding region and the region coding for the secretion signal, all regions being of the neutral protease gene of Bacillus amyloliquefaciens.

Further, this fused DNA sequence of this hybrid plasmid had the above-mentioned DNA sequence (III).

EXAMPLE 2

Secretory production of polypeptide having thrombin inhibiting activity by hirudin secreting plasmid The cells of Bacillus subtilis MT-430 strain (FERM BP-1079) were transformed with plasmid pNPH208 constructed in Example 1 by the method of Chang et al. (see Reference 24). The resultant transformants MT-141 (FERM BP-2403) were cultured using the 2-fold concentrated LB medium by incubating at 37° C. for 20 hours with shaking. The thrombin inhibiting activity of the resultant culture supernatant was measured according to a conventional method.

In the culture supernatant obtained by cultivating at 37° C. for 20 hours using a 2-fold concentrated LB medium, HV1-hirudin having thrombin inhibiting activity of 180 to 200 mg per 1 liter medium was accumulated. This is because the polypeptide in which the N-terminal valine of HV1-type hirudin and aspartic acid at the fifth residue from the N-terminal end were replaced by alanine and glutamic acid, respectively, was excreted more efficiently than HV1-type hirudin. Further, the optical density (A660) of the culture showing this extent of growth of Bacillus subtilis was 10.

SDS-PAGE analysis of the precipitate obtained by adding trichloroacetic acid to the supernatant showed that a large amount of protein of the same size as the hirudin standard obtained by purifying the HV1-type hirudin purchased from Sigma was accumulated in the culture supernatant. Analysis of this protein using a gel-scanner densitometer showed that the amount of the polypeptide having thrombin inhibiting activity present in the culture supernatant of MT-141 strain was as much as 7%. Thrombin inhibiting activity was retained in the supernatant fraction obtained by treating this supernatant at 70° C. for 15 minutes and centrifuging to remove the resulting proteinous precipitate. Further, the yield of the polypeptide having thrombin inhibiting activity was increased to 23% of the total protein and thus the rate of foreign protein contamination was extremely low.

The polypeptide having thrombin inhibiting activity was purified from this supernatant by the method used in Comparative Example 2. Unlike the case of the HV1-type hirudin secretive production as shown in Comparative Example 2, neither secretion nor accumulation of inactive-type hirudin was observed. The obtained polypeptide having hirudin inhibiting activity appeared as a single band on SDS-PAGE and, in addition, had the same molecular weight as the HV1-type hirudin preparation obtained by purifying leech-origin HV1-type hirudin purchased from Sigma. Consequently, using the purified polypeptide so obtained, the N-terminal amino acid sequence was determined, which revealed the sequence Ala-Val-Tyr-Thr-Glu.

From these results, it was determined that the polypeptide produced and secreted by the Bacillus subtilis strain transformed with the secretion plasmid of the present invention was secreted in a form in which the secretion signal was correctly removed. Thrombin inhibition test showed that this purified HV1-type hirudin reacted stoichometrically with thrombin at a ratio 1:1.34.

These results show that the polypeptide which is produced and secreted by the Bacillus subtilis strain transformed with the secretion plasmid of the present invention has the same hirudin inhibiting activity as HV1-type hirudin derived from leeches.

The above-mentioned strains having FERM numbers were deposited with the Fermentation Research Institute of the Agency of Industrial Science and Technology, 1-3, Higashi 1-chome, Tsukuba-shi, Ibaraki-ken, 305, Japan, under the Budapest Treaty.

Each having an FERM number was deposited on the following date:
FERM BP-923 (MT-8400) on Oct. 14, 1985
FERM BP-1985 (MTE-4014) on Mar. 5, 1988
FERM BP-1079 (MT-430) on Jun. 13, 1986
FERM BP-1983 (MT-208) on May 21, 1988
FERM BP-2403 (MT-141) on Apr. 27, 1989

References

1. Rosenberg, R. D., Semin. Hematol., 14, 42–440, 1977
2. Markwardt, F., "Methods in Enzymol." 19, 928–932, 1970
3. Markwardt, F. et al., Thromb. Haemostasis (Stuttgart). 52, 160–163, 1984
4. Badgy, E. et al, "Methods in Enzymol." 45, 669–678, 1976
5. Kenji Owari; Gendai Kagaku, Supplement 10, (Tokyo Kagaku Dojin), pp. 189–196, 1987
6. International Patent Publication No. WO 85/04418
7. Dodt, J. et al., FEBS Lett. 202 (2), 373–377, 1986
8. Naoto Sotouchi et al., Nihon Rinsho (The Japanese Journal of Clinical Medicine) 5, 98–103, 1988
9. Meyhack et al., Thrombosis Research VII 33, 1987
10. Grossenbacher et al., Thrombosis Research VII 34, 1987
11. Palva, I. et al., Proc. Natl. Acad. Sci. USA 79, 5582–5586, 1982
12. Vasantha, N. et al., J. Bacteriol. 165, 837–842, 1986
13. Lin-Fa Wang et al., Gene 69, 39–47, 1988
14. Palva, I. et al., Gene 22, 229–235, 1983
15. Schein, C. H. et al., Bio/Technology 4, 719, 1986

16. Sukmaran et al., Biotechnology 6, 72-77, 1988
17. Rosenberg, M. et al., Ann. Rev. Genet. 13, 319, 1979
18. Moran Jr., C. P. et al., Mol Gen. Genet., 186, 339-346, 1986
19. Goldfarb, D. S. et al., Nature 293, 309, 1981
20. Blobel, G. et al., Cell Biol. 67, 835, 1975
21. Kyoji Yamaguchi et al., Gendai Kagaku, Supplement 10, 3-18, 1987
22. Mao SJT., Biochemistry 27, 8170-8173, 1988
23. Loison, G. et al., Biotechnology 6, 72-77, 1988
24. Chang, S. et al., Mol. Gen. Genet. 168, 111-115, 1979
25. Maniatis, T. et al., "Molecular Cloning", p. 440, Cold Spring Harbor Laboratory, 1982
26. Tabak, H. F. et al., Nucleic Acids Res. 5, 2321-2321, 1978
27. Crea, R. et al., Proc. Natl. Acad. Sci. USA 75, 5765, 1978
28. Goeddel, D. V. et al., Proc. Natl. Acad. Sci. USA 76, 106-110, 1979
29. Ogasawara, N., Gene 40, 145-150, 1985
30. Chang, J., FEBS Lett. 164, 307-313, 1983
31. Hewick, R. M. et al., J. Biol. Chem. 256, 7990-7999, 1981

What is claimed is:

1. A precursor of a polypeptide having thrombin inhibiting activity, having the following amino acid sequence:

Met—Gly—Leu—Gly—Lys—Lys—Leu—Ser—Ser—Ala—Val—Ala—Ala—Ser—Phe—Met—Ser—Leu—Thr—Ile—Ser—Leu—Pro—Gly—Val—Gln—Ala—Ala—Val—Tyr—Thr—Glu—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His—Asn—Asp—Gly—Asp—Phe—Glu—Glu—Ile—Pro—Glu—Glu—Tyr—Leu—Gln.

2. A polypeptide having thrombin inhibiting activity, having the following amino acid sequence:

Ala—Val—Tyr—Thr—Glu—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His—Asn—Asp—Gly—Asp—Phe—Glu—Glu—Ile—Pro—Glu—Glu—Tyr—Leu—Gln.

* * * * *